United States Patent [19]
Meijer et al.

[11] Patent Number: 4,986,654
[45] Date of Patent: Jan. 22, 1991

[54] METHOD AND APPARATUS FOR CONTACTLESS ACQUISITION OF DATA FOR THE LOCALLY RESOLVED DETERMINATION OF THE DENSITY AND TEMPERATURE IN A MEASUREMENT VOLUME

[75] Inventors: Gerard Meijer, Nijmegen, Netherlands; Peter Andresen, Dransfeld, Fed. Rep. of Germany; Gerd E. A. Meier, Roringen, Fed. Rep. of Germany; Hans W. Luelf, Goettingen, Fed. Rep. of Germany

[73] Assignee: Max-Planck-Gesellschaft ... e.V., Goettingen, Fed. Rep. of Germany

[21] Appl. No.: 170,715

[22] Filed: Mar. 21, 1988

[30] Foreign Application Priority Data
Mar. 19, 1987 [DE] Fed. Rep. of Germany ....... 3709065
Aug. 31, 1987 [DE] Fed. Rep. of Germany ....... 3729063

[51] Int. Cl.$^5$ ........................ G01J 5/28; G01N 21/64; G01B 9/025
[52] U.S. Cl. ................................... 356/43; 250/458.1; 250/459.1; 356/318; 356/347; 374/161
[58] Field of Search ...................... 356/43, 45, 73, 317, 356/318, 347; 250/458.1, 459.1, 461.1; 374/161

[56] References Cited
U.S. PATENT DOCUMENTS
4,081,215  3/1978  Penney et al. ......................... 356/45
4,313,057  1/1982  Gelbwachs ....................... 250/458.1

FOREIGN PATENT DOCUMENTS
2544544  4/1977  Fed. Rep. of Germany .

Primary Examiner—Vincent P. McGraw
Attorney, Agent, or Firm—Frishauf, Holtz, Goodman & Woodward

[57] ABSTRACT

Method and apparatus for contactless locally resolved instantaneous measurement of the density and/or temperature of a gas in a measurement volume which can have a relatively large area and a relatively small thickness, wherein by laser radiation two rotational transitions of a molecular constituent of the gas excitation in which the excited state has a life time which is substantially shorter than the reciprocal collision frequency in the gas, and wherein the fluorescence intensity or absorption corresponding to the two rotational transitions is measured. From the measured intensities the density and temperature can be calculated.

20 Claims, 4 Drawing Sheets

METHOD AND APPARATUS FOR CONTACTLESS ACQUISITION OF DATA FOR THE LOCALLY RESOLVED DETERMINATION OF THE DENSITY AND TEMPERATURE IN A MEASUREMENT VOLUME

BACKGROUND OF THE INVENTION

1. Field of the Invention

The present invention relates to a method and apparatus for contactless acquisition of data for the locally resolved determination of the instantaneous density and/or temperature ("density distribution", "temperature distribution") of a molecular gas in a measurement volume which can have a relatively large area and a relatively small thickness by laser-induced fluorescence (LIF).

2. Description of the Prior Art

It is known from the journal CHEMICAL PHYSICS LETTERS Volume 114, No. 5, 6, Mar. 15, 1985, p. 451–455 to excite selectively individual rotational vibrational states of molecular oxygen at pressures up to about 0.4 MPa by laser radiation and to measure the resulting laser-induced fluorescence (LIF).

The use of the known methods operating with laser-induced fluorescence (LIF) for determining densities and temperatures in a gas mixture is problematical at relatively high pressures because the fluorescence intensity is governed substantially by conditions of the laser-excited molecules with the surrounding gas, the so-called "quenching". The quenching depends via the collision parameters, in particular the collision frequency, on the instantaneous gas composition (the partial densities $n_i$ of the components of the gas mixture) and on the temperature LIF is therefore not suitable for example for exact investigations of combustion processes in internal-combustion engines and the like because both the gas composition and the temperature in the combustion chamber are parameters which vary greatly depending on the location and time and the quenching is therefore also a complicated function dependent on location and time and basically not known.

SUMMARY OF THE INVENTION

The present invention is based on the problem of providing methods and apparatuses with which the density and/or the temperature of a component of a gas in a measurement volume can be instantaneously resolved in time even at relatively high pressures and can be exactly measured.

This problem is solved according to the invention in that by laser radiation at least one molecular rotational transition of a molecular component of the gas is excited and that the fluorescence from the excited rotational transition or the absorption by said transition is detected during a period of time which is substantially shorter than the reciprocal collision frequency in the gas.

In a preferred embodiment of the present method a molecular rotational transition is excited which has a substantially shorter life time than the reciprocal collision frequency.

Preferably a gas is used which contains molecules which, in the electronically excited state, predissociate. The fluorescence radiation emitted by these molecules during the predissociation life time is measured.

The life time of the excited state can be shortened by laser-induced depopulation, e.g. ionization.

Finally, the objective of being able to measure for density and/or temperature determination a laser-induced fluorescence radiation uninfluenced by collisions (quenching) can also be achieved in that the fluorescence is excited by a very steep and short laser radiation pulse having a duration which is short compared with the reciprocal collision frequency in the measurement volume and which can lie in the picosecond range and limiting the detection duration of the fluorescence by electronic measures such as sampling of the radiation receiver and/or the fluorescence or absorption signal processing means, to a period of time in which collision processes in the gas have no appreciable influence on the fluorescence intensity or absorption.

The present method makes it possible to measure the density and/or temperature in a volume which may be thin and flat, i.e. "sheet-like", even at relatively high pressures instantaneously (momentarily) in locally resolved and exact manner.

By employing rapidly predissociating states, i.e. states in which the predissociation rate is considerably greater than the quenching rate, a fluorescence signal is obtained which is not falsified by quenching. The method therefore permits an error-free contactless measurement of absolute and relative densities.

Therefore, in preferred embodiments of the invention in the LIF only molecular transitions which predissociate in the electronically excited state and thus have an extremely short life time $\tau_p$ are used. The predissociation life time $\tau_p$ of many molecules is at relatively high energies (short wavelength) substantially shorter than the radiation life time $\tau_r$. Since such molecules can emit light substantially only during the short period $\tau_p$ the fluorescence is not disturbed by collisions because in the very short time $\tau_p$ hardly any collisions occur even at high pressures. For $H_2O$ the life time $\tau_p$ is of the order of magnitude of a few picoseconds (trillionths of a second). It is thus possible by means of LIF of $H_2O$ to carry out measurements at pressures up to 5 MPa without fluorescence quenching. In the case OH $\tau_p$ is of the order of magnitude of 100 psec so that fluorescence quenching is negligible up to pressures of about 0.1 MPa.

The method can for example be used for rendering visible time and space density and/or temperature distributions or variations in combustion operations, such as in petrol engines, and also to represent flows or to measure air contaminations as employed with the aid of the LIDAR method. In this case with at least one pair of time-displaced laser excitation pulses the density of a predetermined quantum state is measured in the measurement field at different instants and it is thereby possible to determine the change in the topology in the measurement field. In the investigation of turbulent flows, for example in combustion processes, the time interval between the two excitation pulses may be of the order of magnitude of microseconds. Generally the time interval between the two excitation pulses will be chosen so that on the one hand the desired time resolution is obtained and on the other the topology is still recognisable.

Hereinafter preferred embodiments of the invention will be explained in detail with reference to the drawings.

DETAILED DESCRIPTION OF PREFERRED EMBODIMENTS

The term "molecule" here is meant to cover both molecules in the narrower sense, such as $H_2O$ and $O_2$, and multi-atom, in particular two-atom, molecule parts or radicals such as OH.

Firstly, the principle of the method according to the invention will be explained with the aid of the simplified energy level scheme in FIG. 1. With a laser a molecule (hereinafter also referred to as "tracer molecule") is excited out of a quantum state 1 into a quantum state 2 with an excitation rate $\eta$. With the tracer molecule selected the quantum state 2 undergoes losses due to (a) fluorescence at a total rate $\bar{k}_f$,
(b) predissociation at a rate $k_p$ and
(c) quenching by collisions at a rate Q.

Figure 1:
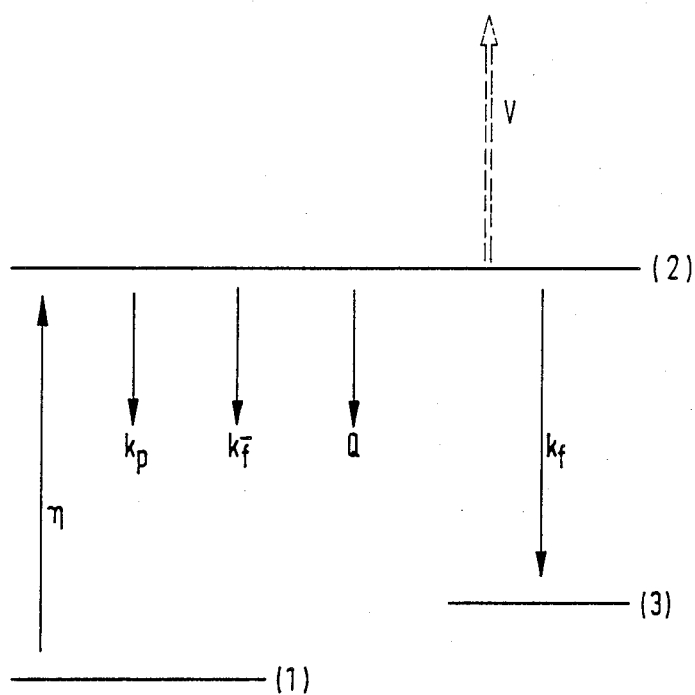
FIG. 1 is an energy level diagram of a fluorescence excitation.

Part of the fluorescence, corresponding in FIG. 1 to the transition from the quantum state 2 to the quantum state 3, is measured with suitable detection methods (e.g. photomultiplier or image intensifier). The rate of this fluorescence component to be measured is designated by $k_f$.

Firstly, the measurement of the density $n_1$ of the tracer molecule in the quantum state 1 will now be discussed. For the special case of an excitation rate $\eta$ from the quantum state 1 to the quantum state 2 which is not too great the time variation of the density in the state 2 can be calculated and this gives by integration of the radiation time $\tau$ with respect to time:

$$\int n_2(t)\, dt = \frac{\eta\, n_1\, \tau}{k_p + k_f + Q} \qquad (1)$$

This gives for the fluorescence F from state 2 to state 3:

$$F = \frac{k_f}{k_p + k_f + Q}\, \eta\, n_1\, \tau \qquad (2)$$

In contrast to previously used LIF methods at high pressures in this case (because of the choice of a tracer molecule predissociated in the stimulated state) the predissociation occurs as an important term.

Without predissociation ($k_p = 0$) we have $$F = \frac{k_f}{k_f + Q}\, \eta\, n_1\, \tau \qquad (3)$$

At atmospheric pressure the quench rate is in the range $10^9$–$10^{10}$/sec whilst the fluorescence rate $k_f$ lies in the range $10^6$–$10^8$/sec. Consequently, $k_f$ can be neglected compared with Q and this gives $$F = \frac{k_f}{Q}\, \eta\, n_1\, \tau \qquad (4)$$

The fluorescence is therefore inversely proportional to the quench rate Q. To determine the density $n_1$ in this case ($k_p = 0$) it is necessary to know the quench rate Q which in particular for example in turbulent combustion systems is very much dependent on the gas composition, the temperature and the corresponding rate constants for the collisions of various molecules with the tracer molecule in the quantum state 1. Local and time variation of this quantity therefore makes a precise determination of the density $n_1$ practically impossible.

In contrast, in the case according to the invention of rapid predissociation $k_p \gg Q + k_f$ holds and this gives:

$$F = \frac{k_f}{k_p}\, \eta\, n_1\, \tau \qquad (5)$$

In the case of linear approximation the following holds for the excitation rate $$\eta\tau = \bar{\sigma} I \tau \qquad (6)$$

$I.\tau$ is the number L of the photons per $cm^2$ and $sec^{-1}$ and $\sigma$ is the integrated absorption coefficient. This gives:

$$F = \frac{\bar{\sigma}\, k_f}{k_p}\, L\, n_1 \qquad (7)$$

The essential difference to equation (4) is that the collisions play no part. The fluorescence to be measured is now linked to the density $n_1$ only via the measurable quantity L and via molecular constants.

The method according to the invention is thus based primarily essentially on shortening the life of the excited state so that the quenching rate becomes negligibly small. In the example of embodiment described above this shortening is done by predissociation.

Another method of shortening the life is the depopulation from quantum state 2 by a laser or other corresponding light source. An example preferred at present is ionization from quantum state 2.

For intensive lasers the loss rate V from the excited state may also be made larger than the quench rate. Fluorescence is then emitted only during the life shortened by the laser. The advantage of this method resides in that the life can be preselected via the laser.

Figure 2:
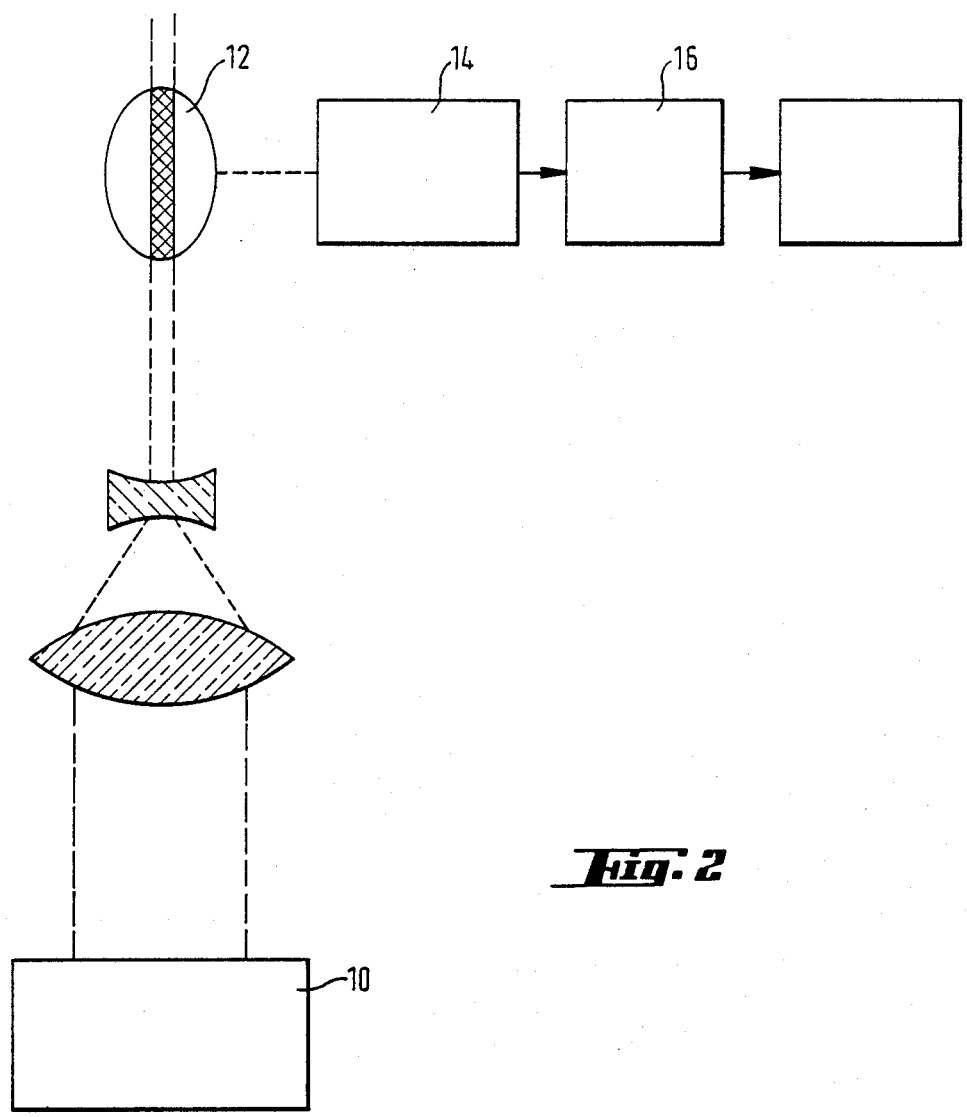
FIG. 2 is a schematic fundamental illustration of an apparatus for carrying out the present method.

As illustrated schematically in FIG. 2 with the present method with a tunable laser 10 a measurement volume 12 is irradiated in which a molecular gas is disposed whose density distribution is to be determined. The term "molecular gas" is also to include gas mixtures containing a suitable molecular component, i.e. for example combustion gases containing corresponding "tracer molecules". In the test or measurement volume various molecular transitions of molecules (molecule lines) in the gas, preferably OH or $H_2O$, which in practice are usually present, are excited to fluorescence at various frequencies by laser radiation. In general transitions are preferred at which both the electronic quantum number and the rotational quantum number and possibly also the vibrational quantum number change. If the gas itself does not contain any molecular type suitable for LIF measurement then such a molecular type can be added for the purpose of the measurement. The fluorescence intensity is a measure of the occupation of the state (starting state) from which the excitation is effected. If for example stimulation is at a frequency $\nu_1$ from the rotational state $j_1$ the fluorescence intensity is proportional to the density of the particles in the rotational state $j_1$. The fluorescence intensity is measured resolved locally (x, y) over the area of the measurement volume, in time (t) and spectrally (λ), i.e. $I = I(x, y; t, \lambda)$ is measured. For this purpose the fluorescence light is split up spectrally for example by a wavelength-selective means 14, for example by a filter or spectrometer, and detected momentarily with a locally sensitive and time-resolving means 16, such as a photographic or photoelectronic camera, e.g. a sampled image intensifier with following CCD (Charge Coupled Device) camera.

If the fluorescence F is measured with a calibrated means an absolute determination of the density can be made. With a locally resolving detecting means (e.g. image intensifier) the density $n_1$ can be measured locally resolved. For relative density measurements (e.g. density at various locations) calibration is not necessary.

In the method outlined so far the density is measured only in one quantum state. If the partial density of the tracer molecule is to be measured not only in the quantum state 1 but entirely then the temperature must also be measured with the method described below. This further improvement of the method can accordingly also be used for instantaneous locally resolved temperature measurement.

The measurement of the fluorescence intensity is thus carried out for two different frequencies at which different rotational lines $j_1$, $j_2$ are excited. From the corresponding fluorescence intensities $I_1(x,y; t_1, \lambda_1)$ and $I_2(x, y; t_2, \lambda_2)$ at the frequencies $(\nu_1)$ and $(\nu_2)$ the temperature field (the local temperature distribution in the measurement volume) can be calculated $t_1$, $t_2$ or $\lambda_1$, $\lambda_2$ indicate that the fluorescence can be analyzed at various times or at various wavelengths.

The determination of the temperature is based on the distribution, in thermal equilibrium, amongst the rotational states being given by Boltzmann's constant:

$$P_j = A(2j + 1)e^{-E_j/kT} \qquad (8)$$

Where
k is Boltzmann's constant,
$E_j$ is the energy of the rotational state J and
A is a scaling factor.

If the occupation of two rotational states (quantum numbers $j_1$, $j_2$) are measured by LIF the temperature is obtained from the fluorescence intensities $I_1(x, y; t, \lambda_1)$ at $j_1$ and $I_2(x, y; t, \lambda_2)$ at $j_2$ as:

$$T(x,y;t) = \frac{(E_{j2} - E_{j1})}{k \ln\left(\frac{(2j_2 + 1)}{(2j_1 + 1)} \frac{I_1(x,y;t,\lambda_1)}{I_2(x,y;t,\lambda_2)}\right)} \qquad (9)$$

Thus, the temperature field T(x, y; t) can thus be obtained resolved locally and in time. The time resolution results from the short-duration emission (triggering) of the laser.

The fluorescence intensities $I_1$, $I_2$ must be determined separately for the two frequencies. For this purpose two different lasers can be used which are pulse-activated with a small delay. The one laser is operated at the frequency $\nu_1$, the other at the frequency $\nu_2$. The delay between the two laser pulses is made so small that no movements occur in the sample to be analyzed (e.g. 100 nsec). $I_1$ and $I_2$ are measured only during the laser pulses and can thus be measured separately by time resolution.

With certain molecules (e.g. OH) a laser may also be used which emits simultaneously at two or more frequencies (e.g. with a broad-band laser). In this case the separate measurement of $I_1$ and $I_2$ is also possible through the different spectral position of the fluorescence With a laser whose radiation contains the two frequencies and $\nu_1$ and $\nu_2$ two rotational lines are again stimulated. The fluorescence is spectrally analyzed At the wavelength $\nu_1$ the fluorescence intensity $I_1(x, y; t, \lambda_1)$ caused by the frequency component at $\nu_1$ is measured and at the wavelength $\lambda_2$ the fluorescence intensity $I_2(x, y; t, \lambda_2)$ caused by the frequency component at $\nu_2$. The spectral analysis can be made with spectrometers or filters.

When the temperature field is known the Boltzmann distribution gives for the occupation of the quantum state j:

$$n(j) = n A_0 (2j+1) \exp(-E_j/kT) \qquad (10)$$

with the total density n of the tracer molecule. Assuming that for the quantum state 1, $n_1$ is measured and the temperature is known. This therefore gives:

$$n = \frac{n(j_1)}{A_0 (2j_1 + 1) \exp(-E_{j1}/kT)} \qquad (11)$$

$A_0$ is a scaling constant theoretically determinable for the temperature measured.

Consequently, by measuring the temperature on two rotational lines the density can be directly determined as well.

EXAMPLE

In a test a gas containing free OH (open atmospheric flame) under atmospheric pressure and a tunable KrF-Excimer laser (248.0–248.9 nm) were used. The OH was excited in this frequency range from $^2\pi$ to $^2\Sigma$, from v"=0 to v'=3. This vibrational transition was excitation for the first time with a laser. A whole number of rotational lines were identified, inter alia (R$_2$(15), Q$_2$(11), Q$_2$(10), Q$_1$(11), Q$_1$(10), R$_1$(15), O$_2$(6), P$_2$(8), P$_1$(8), R$_2$(14). The fluorescence was spectrally analyzed Various bands occur in emission which are partially disturbed by quenching and partially not disturbed by quenching. Direct fluorescence is observed from v'=3 to v"=3 (v"=2; v'=1) at λ=325 nm (294 nm; 268 nm). This fluorescence is not disturbed by quenching because the life in the state v'=3 is very short ($\approx$100 psec). Withing this short time only a slight redistribution by collisions takes place in the electronically excited $^2\Sigma$ state. This has been directly verified: At these wavelengths (325, 294, 268 nm) individual rotational lines (P, Q, R) occur in emission. The redistribution to other rotational states at normal pressure is less than 10%. In contrast, in the fluorescence from v'=2,1,0, which occurs at various other wavelengths (287, 318, 281, 312, 306 nm), a great number of rotational lines appear Due to the longer life time $\tau_p$ quenching plays a far greater part here. Consequently with OH only direct fluorescence from v'=3 is suitable at high pressures. A substantial advantage of the method is thus based on the utilization of the very rapid predissociation from higher vibrational states which is also to be observed with many other molecules likewise at short wavelengths.

The spectral analysis is important here because various fluorescent molecules are excited simultaneously. Only spectral discrimination of the fluorescence permits unequivocal identification of the individual molecules.

The same measures can be employed for example within the same spectral range (248.0–248.9 nm) for the molecules $H_2O$ and $O_2$ as well. With $H_2O$ the C state is reached with two-photon excitation. The life $\tau_p$ of the C state is $\leq 5$ psec.

During this life an emission takes place from the C state to the A state (380–600 nm). In complete analogy to OH hardly any collisions occur in the very short life $\tau_p$. The fluorescence is not quenched even at relatively high pressures, e.g. up to 2 MPa, and permits measurements at even higher pressures than with OH.

In the tuning range of the KrF laser there are a number of oxygen lines of the vibrational transition $v''=6$ to $v'=0$ (R lines: j=9,11,13,15,17,19; P lines: j=7,9,11,13,15) and of the vibrational transition from $v''=7$ to $v'=2$ (R lines: j=7,9,11,13,15; P lines: j=5,7,9,11) which are suitable for the present method.

The use of a tunable KrF laser has the substantial advantage over conventional lasers that the power is substantially greater (about 1000 times in this spectral range). In spite of this high power and good focussing the single-photon transition for OH ($^2\Pi, v''=0 -> ^2\Sigma, v'=3$) is not yet saturated because the Franck-Condon factor for this transition is very small. Consequently, adequate excitation of $v'=3$ can generally only be reached with such strong lasers. The situation is similar with $H_2O$. Even powers of the order of 4 $J/cm^2$ do not lead to saturation here. A substantially weaker laser suffices for $O_2$ because these transitions are completely saturated even at $<100$ $mJ/cm^2$. The strong laser permits exposure of a larger area so that nevertheless from each point of the area the amount of light emitted suffices to permit analysis of the intensity distribution for individual laser pulses.

Some important points of the preferred embodiment of the present method explained above will now be again briefly summarized:

(1) Due to the very short life of the $^2\Sigma(v'=3)$ state of the OH the method of LIF can also be used for high pressures. The same applies to $H_2O$ and $O_2$, (2) In some cases (e.g. OH) with a broad-band laser the temperature field can be determined by spectral analysis of the fluorescence.

(3) By using a tunable Excimer laser a large-area exposure with high excitation degree can be achieved even for weakly-absorbing molecules.

Below some apparatuses for carrying out various embodiments of the present method will be described which are particularly expedient for practical use.

Figure 3:
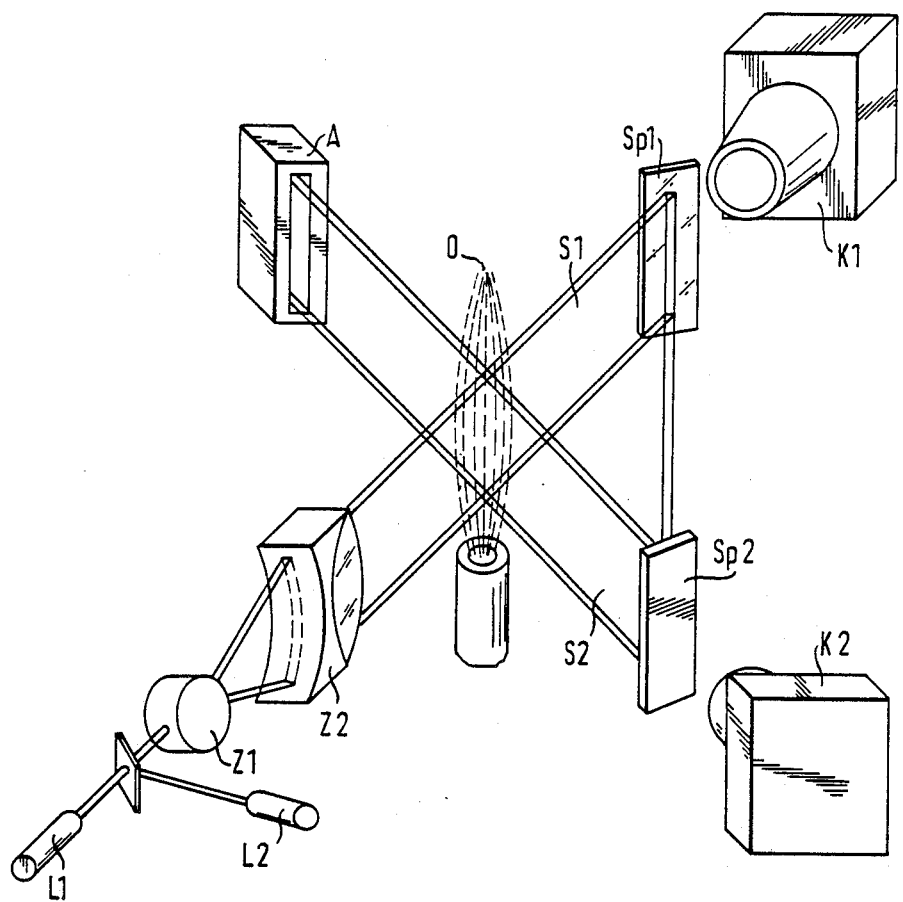
FIGS. 3, 4 and 5 each show a schematic representation of a practical embodiment of an apparatus according to the invention for carrying out the present method.

As shown by FIG. 3 a spatial measurement volume or object 0 can be traversed by two portions S1 and S2 of a for example strip-like light beam, said portions intersecting each other at an angle of 90°. The strip-like light beam which passes through the object 0, represented as flame, can be generated using a cylindrical lens collimator arrangement Z1, Z2 and selectively reflecting mirrors $Sp_1$, $Sp_2$ which reflect the laser radiation but allow fluorescence radiation to pass through. With two cameras K1 and K2 which detect the fluorescent light allowed through by the mirror $Sp_1$ or $Sp_2$ an approximate spatial density distribution in the object 0 can be determined by registering two for example orthogonal sections. The cameras are preferably electronic image intensifier cameras which operate with high picture repetition rate so that the image pairs required for the method can be picked up corresponding to the intensity of two different fluorescence lines with short time interval. For fluorescence excitation two lasers L1, L2 can be used which flash in quick succession with different excitation frequencies. The fluorescence radiation can also be simultaneously excited and then spectrally split up to detect the lines of interest. The laser radiation beam S2 is finally absorbed in an absorber A.

Figure 4:
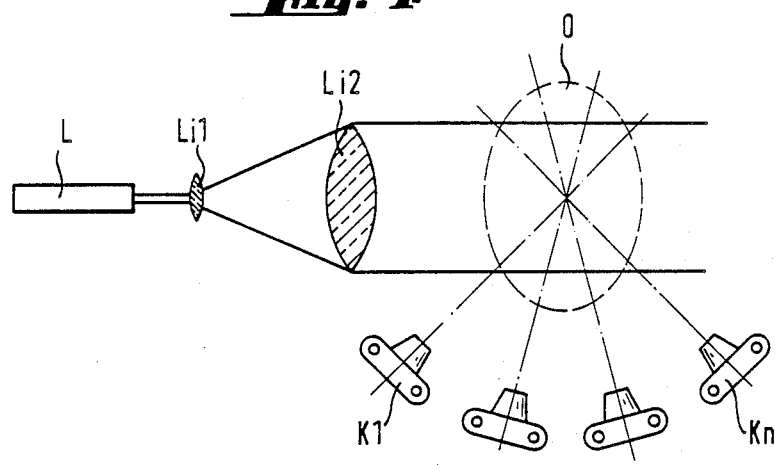

In the apparatus according to FIG. 4 the measurement volume or object 0 is traversed with a laser radiation beam which is generated by means of a laser L and a beam diverging optical means comprising two collecting lenses Li1 and Li2 . To obtain a complete spatial resolution the fluorescent gas in the measurement volume or object 0 is simultaneously picked up by several cameras K1 to Kn so that a tomographic reconstruction of the spatial intensity distribution is possible, for example by a so-called Radon Transformation.

In all the methods hitherto referred to it is conceivable for the time resolution of the density or temperature changes to take film exposures of the fluorescent light. If a continuous time resolution is desired so-called streak exposures appear expedient.

Figure 5:
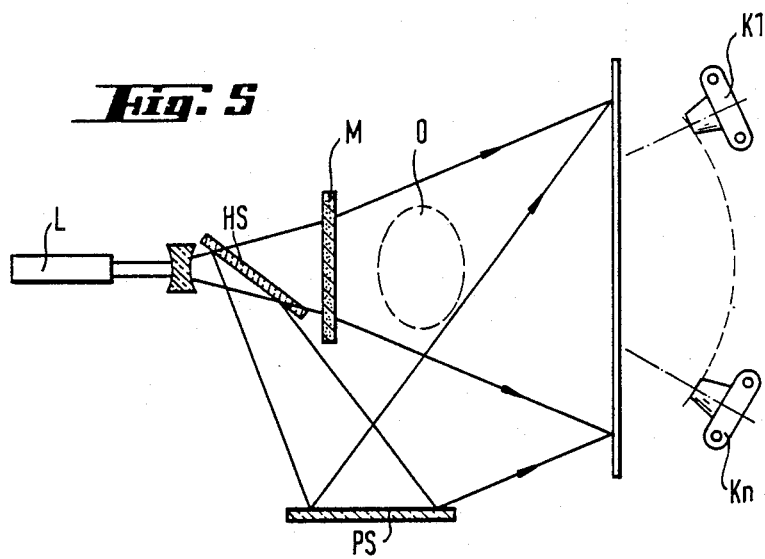

FIG. 5 shows an apparatus for density measurement operating with a holographic method. In this embodiment of the present method the fluorescence generated by the excitation of the molecules is not utilized but only the absorption of the excitation line in the gas in the measurement volume or object 0. The apparatus according to FIG. 5 includes a laser L whose exit radiation beam is made divergent by a concave lens and split by a beam splitter such as a semi-transparent mirror HS into an object beam and a reference beam coherent therewith. The object beam passes through a ground-glass disc M and through the object 0 onto a hologram plate H , e.g. a photographic plate, while the reference beam is projected by a plane mirror PS around the object 0 onto the hologram plate. The absorption effects a phase shift of the excitation light passing through the object in the object beam. This apparatus is now employed together with several cameras K1 to Kn to measure the temperature distribution in the object by a so-called double-exposure hologram.

In the production of a double-exposure hologram the hologram plate H is actually illuminated simultaneously with a radiation beam passing through the object and a coherent reference beam conducted round the object. This gives a first hologram. The same operation is then repeated at any desired (subsequent) instant (with another object). After development of the hologram plate exposed twice in this manner a reconstruction then shows interference fringes which correspond generally to the phase difference of the two objects. If in the first exposure a so-called zero object is employed, that is for example the empty apparatus, then only the properties of the apparatus are stored in the first hologram. If now in the second exposure any desired object 0 is introduced into the object beam path as subsequent reconstruction the pure phase structure of the object 0 is obtained. Any amplitude structure of the object is also reproduced. This is however overlaid by spurious radiation depending on the property of the zero object.

Phase shifts of the object 0 in different transmission directions can be rendered visible with the aid of the cameras K1 to Kn in the form of interference fringes. These phase displacements are however always the integral phase shift of the light in the entire object 0. If it is desired to obtain the spatial density distribution of the object 0 by a tomographical reconstruction the local density values must be calculated from these different density integrals. This method is referred to as holographic or interferometric tomography.

By the double-exposure hologram explained above not only the phase difference between a zero object and the object 0 of interest can be rendered visible but equally well the phase difference between two objects 01 and 02. For this purpose in a first hologram exposure the object 01 is exposed and then at any later instant or also simultaneously with a second laser the hologram 02 is exposed on the hologram plate. This difference method of the first type is modified for the present purpose only in that for the second hologram which is exposed in the double-exposure method on the hologram plate a different laser frequency is employed. The reconstruction of such a difference hologram following the development then exhibits a trivial pattern for the difference frequency of the laser frequencies (i.e. a system of concentric circles or approximately parallel fringes) which is additionally deformed by the different phase responses of the two frequences F1 and F2 in the object. Thus, by evaluating these interferograms the different phase rotation of the light for the two light frequencies F1 and F2 can be stored in a hologram. With two difference holograms of this type it is then possible to determine the temperature distribution in the object in the following manner:

From the first difference hologram the density difference $n_2 - n_1$ is obtained for two rotational states $j_2$, $j_1$ at the frequencies $\nu_2$ and $\nu_1$ in accordance with Boltzmann's law $$n_2 - n_1 = A \cdot \{(2j_2+1)e^{-E_2/kT} - (2j_1+1)e^{-E_1/kT}\}. \quad (12)$$

The second difference hologram furnishes the density difference $n_{3-n_1}$ for a further rotational state $j_3$ at the frequency $\nu_{3}$ relative to the rotational state $j_1$:

$$n_3 - n_1 = A \cdot \{(2j_3+1)e^{-E_3/kT} - (2j_1+1)e^{-E_1/kT}\}. \quad (13)$$

The quotient R of the measured density differences then permits determination of the temperature numerically from the following equation with the one unknown T:

$$R = \frac{n_2 - n_1}{n_3 - n_1} = \frac{(2j_2+1)e^{-E_2/kT} - (2j_1+1)e^{-E_1/kT}}{(2j_3+1)e^{-E_3/kT}(2j_1+1)^{-E_1/kT}} \quad (14)$$

For the present method other molecule types may also be used, for example CH, NH, SH, NO.

The meaning of the term "molecular rotational transition" is not limited to transitions in which only the rotational quantum number changes, but includes also transitions in which the rotational quantum number and further the electronic quantum number and/or the vibrational quantum number change.

We claim:

1. A method for contactless acquisition of data for determining at least one of the parameters density and temperature of a molecular gas within a predetermined volume, said gas containing molecules which collide with each other with a predetermined collision frequency, said method comprising the steps:
    (a) directing laser radiation adapted to excite at least one molecular rotational transition of said gas molecules through said volume to produce excited molecules, and
    (b) measuring the density of said excited molecules during a period of time after said excitation step (a) which is substantially shorter than the reciprocal of said collision frequency.

2. The method as claimed in claim 1 wherein said step (a) comprises exciting a molecular rotational transition of said molecules which has a lifetime substantially shorter than the reciprocal of said collision frequency.

3. The method as claimed in claim 1 wherein
    said measuring step (b) comprises the step of measuring a fluorescence radiation emitted by said excited molecules.

4. The method as claimed in claim 1 wherein
    said measuring step (b) comprises the step of measuring the optical absorption of said excited molecules.

5. The method as claimed in claim 1 wherein
    said excited molecules predissociate in an electronically excited state, said predissociated state having a predetermined predissociation lifetime, and
    said measuring step (b) comprises the step of measuring the fluorescence radiation emitted by the excited molecules during said predissociation lifetime.

6. The method as claimed in claim 5 wherein
    said step of measuring fluorescence radiation comprises measuring said radiation at a plurality of wavelengths.

7. The method according to claim 5 wherein
    said molecular gas contains a composition selected from the group consisting of $H_2O$ and OH.

8. The method as claimed in claim 7 wherein step (a) comprises the step of exciting state $v'=3$ of OH, and step (b) comprises the step of measuring direct fluorescence of OH from the excited state $v'=3$.

9. The method as claimed in claim 1 wherein said molecular gas contains a diatomic compound.

10. The method as claimed in claim 4 wherein
    said measuring step (b) comprises the step of holographically measuring the absorption of at least two excitation lines of said excited molecules, each of said lines corresponding to a transition having initial and final states; each initial state having electronic and rotational and vibrational quantum numbers which are different than that of the corresponding final state.

11. The method as claimed in claim 10 wherein
    said halographic measuring step comprises producing a double-exposure halogram.

12. The method of claim 1 further comprising the step of shortening the life of the excited state of the molecules by laser-induced depopulation.

13. The method as claimed in claim 1 wherein step (a) comprises the step of directing a laser radiation pulse through said volume, said pulse having a duration which is short compared with the reciprocal collision frequency of the molecules, and that said measuring step (b) comprises the step of electronically limiting the duration of measuring to a period which is short compared with the reciprocal collision frequency.

14. An apparatus for contactless acquisition of data for determining at least one of the parameters density and temperature of a molecular gas within a predetermined volume, said gas containing molecules which collide with each other with a predetermined collision frequency, said apparatus comprising:
    (a) laser means for generating and directing laser radiation through said volume, said laser radiation containing at least one wavelength adapted to excite a molecular transition of the molecules to produce excited molecules;

(b) optical means for measuring the absorption of said excited molecules during a period of time after said excitation which is short compared with the reciprocal collision frequency.

15. The apparatus as claimed in claim 14 wherein said absorption measuring means comprises halographic recording means.

16. The apparatus as claimed in claim 14 wherein said means for producing said laser radiation comprises means for producing a strip-shaped radiation beam.

17. The apparatus as claimed in claim 14 wherein said laser means produces radiation for exciting state $v'=3$ of OH.

18. An apparatus for contactless acquisition of data for determining at least one of the parameters density and temperature of a molecular gas within a predetermined volume, said gas containing molecules which collide with each other with a predetermined collision frequency, said apparatus comprising:

(a) laser means for generating and directing laser radiation through said volume, said laser radiation containing at least one wavelength adapted to excite a molecular transition of the molecules to produce excited molecules;

(b) means for measuring the intensity of fluorescence radiation emitted by said excited molecules during a period of time after said excitation which is short compared with the reciprocal collision frequency.

19. The apparatus as claimed in claim 18 wherein said means for producing said laser radiation comprises means for producing a strip-shaped radiation beam.

20. The apparatus as claimed in claim 18 wherein said laser means produces radiation for exciting state $v'=3$ of OH.

* * * * *